United States Patent
Finger

(10) Patent No.: US 10,799,652 B2
(45) Date of Patent: Oct. 13, 2020

(54) NEBULIZER DEVICE

(71) Applicant: Convexity Scientific Inc., Fairfield, CT (US)

(72) Inventor: Ralph Finger, Westport, CT (US)

(73) Assignee: Convexity Scientific Inc., Fairfield, CT (US)

( * ) Notice: Subject to any disclaimer, the term of this patent is extended or adjusted under 35 U.S.C. 154(b) by 830 days.

(21) Appl. No.: 14/990,338

(22) Filed: Jan. 7, 2016

(65) Prior Publication Data

US 2016/0199594 A1 Jul. 14, 2016

Related U.S. Application Data

(60) Provisional application No. 62/101,193, filed on Jan. 8, 2015.

(51) Int. Cl.
*A61M 15/00* (2006.01)
*A61M 11/00* (2006.01)
(Continued)

(52) U.S. Cl.
CPC ...... *A61M 11/005* (2013.01); *A61M 15/0023* (2014.02); *A61M 15/0065* (2013.01);
(Continued)

(58) Field of Classification Search
CPC ........ A61M 11/00; A61M 11/001–008; A61M 11/02–08; A61M 15/00–001;
(Continued)

(56) References Cited

U.S. PATENT DOCUMENTS

| 151,570 A | 6/1874 | Crumb |
|---|---|---|
| 3,580,249 A | 5/1971 | Takaoka |

(Continued)

FOREIGN PATENT DOCUMENTS

| CN | 101130121 | 2/2008 |
|---|---|---|
| CN | 101426531 | 5/2009 |

(Continued)

OTHER PUBLICATIONS

European Patent Office, International Search Report in related application No. PCT/US2016/012468, dated Jun. 17, 2016, 8 pages.
(Continued)

*Primary Examiner* — Samchuan C Yao
*Assistant Examiner* — Ned T Heffner
(74) *Attorney, Agent, or Firm* — Schwegman Lundberg & Woessner, P.A.

(57) ABSTRACT

In one embodiment, the present disclosure provides a portable nebulizer comprising a housing, a mouthpiece, a reservoir, a disk having multiple pores, and a unit that is configured to cause the disk to vibrate, wherein the vibration of the disk creates a pressure differential that causes a fluid from the reservoir to move through the disk to create an aerosol for delivery. In one embodiment, the mouthpiece may be held in place with at least one metal plate imbedded in the mouthpiece and at least one magnet imbedded in the housing. In one embodiment, the reservoir may have a non-cylindrical shape. In one embodiment, the nebulizer may comprise a battery and a USB port for charging the battery.

17 Claims, 10 Drawing Sheets

Figure 1:
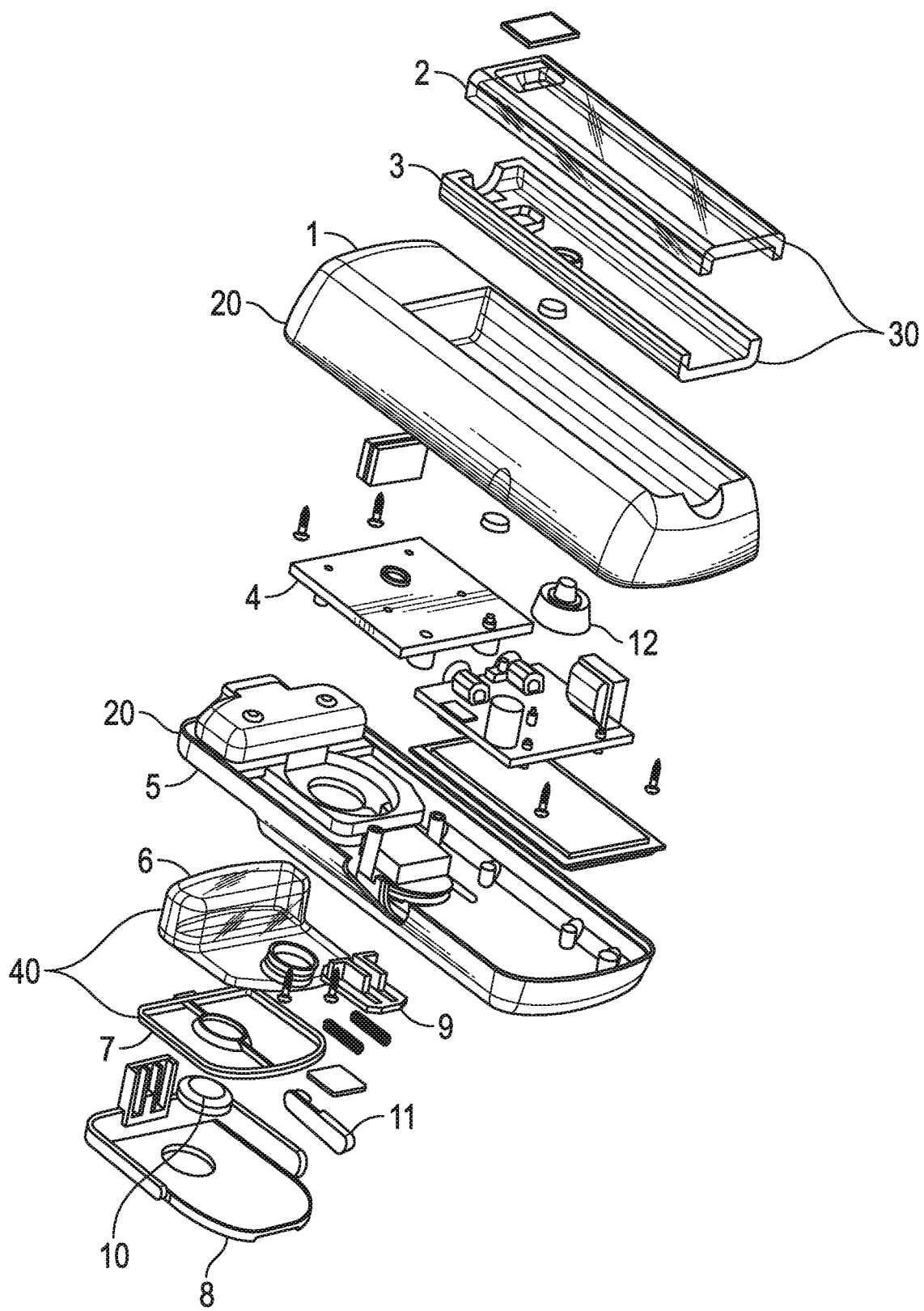

(51) Int. Cl.
  B05B 17/00 (2006.01)
  B05B 11/00 (2006.01)
(52) U.S. Cl.
  CPC ..... *A61M 15/0085* (2013.01); *B05B 11/0054* (2013.01); *B05B 17/0646* (2013.01); *A61M 2205/8206* (2013.01); *A61M 2205/8237* (2013.01); *A61M 2206/14* (2013.01)
(58) Field of Classification Search
  CPC .......... A61M 15/0028; A61M 15/0065–0078; A61M 15/0085; A61M 15/009; A61M 15/06; A61M 15/08; A61M 15/085
  See application file for complete search history.

(56) References Cited

U.S. PATENT DOCUMENTS

| | | | |
|---|---|---|---|
| 3,738,574 A | 6/1973 | Guntersdorfer et al. | |
| 3,790,079 A | 2/1974 | Berglund et al. | |
| 3,812,854 A | 5/1974 | Michaels et al. | |
| 4,094,317 A | 6/1978 | Wasnich | |
| 4,113,809 A | 9/1978 | Abair et al. | |
| 4,119,096 A | 10/1978 | Drews | |
| 4,173,977 A | 11/1979 | Burns | |
| 4,300,546 A | 11/1981 | Kruber | |
| 4,632,311 A | 12/1986 | Nakane et al. | |
| 4,702,418 A | 10/1987 | Carter et al. | |
| 4,776,990 A | 10/1988 | Verity | |
| 5,152,456 A | 10/1992 | Ross et al. | |
| 5,198,157 A | 3/1993 | Bechet | |
| 5,261,601 A | 11/1993 | Ross et al. | |
| 5,297,734 A | 3/1994 | Toda | |
| 5,904,139 A * | 5/1999 | Hauser | A61M 15/009 128/200.14 |
| 6,158,431 A | 12/2000 | Poole | |
| 6,196,218 B1 | 3/2001 | Voges | |
| 6,443,146 B1 | 9/2002 | Voges | |
| 6,629,524 B1 | 10/2003 | Goodall et al. | |
| 6,732,731 B1 | 5/2004 | Tseng | |
| 7,350,520 B1 * | 4/2008 | Richard-Bey | A61M 11/06 128/200.14 |
| 7,954,486 B2 | 6/2011 | Papania et al. | |
| 8,291,902 B2 | 10/2012 | Abrams | |
| 8,387,895 B2 * | 3/2013 | Stangl | A61M 15/0085 128/200.14 |
| 8,616,195 B2 | 12/2013 | Power et al. | |
| 8,910,625 B2 | 12/2014 | Mullinger et al. | |
| 9,022,027 B2 | 5/2015 | Addington et al. | |
| 2005/0016528 A1 * | 1/2005 | Aslin | A61M 15/0091 128/200.23 |
| 2008/0122903 A1 | 5/2008 | Yu et al. | |
| 2009/0223513 A1 * | 9/2009 | Papania | A61M 15/0065 128/200.16 |
| 2009/0241949 A1 * | 10/2009 | Smutney | A61M 15/0015 128/203.15 |
| 2010/0078013 A1 | 4/2010 | Power et al. | |
| 2010/0307497 A1 * | 12/2010 | Busch | A61M 16/0816 128/204.18 |
| 2013/0291865 A1 | 11/2013 | Jones et al. | |
| 2014/0102451 A1 | 4/2014 | Jones et al. | |
| 2014/0209096 A1 * | 7/2014 | Cheyene | A61M 15/08 128/203.12 |

FOREIGN PATENT DOCUMENTS

| | | |
|---|---|---|
| DE | 102005039502 | 2/2007 |
| EP | 0028929 | 5/1981 |
| EP | 0261649 | 3/1988 |
| GB | 2398250 A | 8/2004 |
| KR | 101059479 | 8/2011 |
| KR | 101244233 B1 | 3/2013 |
| RU | 129400 U1 | 6/2013 |
| TW | M487087 | 10/2014 |
| WO | 9416759 | 8/1994 |
| WO | 2006/082941 A1 | 8/2006 |
| WO | 2007028203 | 3/2007 |
| WO | 2010031130 | 3/2010 |
| WO | 2011/083380 A1 | 7/2011 |
| WO | 2013164253 A1 | 11/2013 |

OTHER PUBLICATIONS

"Australian Application Serial No. 2016223288, First Examination Report dated Oct. 17, 2019", 5 pgs.
"Chinese Application Serial No. 201680014746.5, Office Action dated Nov. 27, 2019", w/o English Translation, 2 pgs.
"Chinese Application Serial No. 201680014746.5, Office Action dated Feb. 26, 2020", w/ English Translation, 29 pgs.
"Australian Application Serial No. 2016223288, Examination Report dated May 11, 2020", 5 pgs.
"Taiwanese Application Serial No. 105100428, Response filed Dec. 23, 2019 to Office Action", w/ English Claims, 40 pgs.
"Chinese Application Serial No. 201680014746.5, Response filed Jan. 19, 2020 to Office Action dated Nov. 27, 2019", w/o English Translation, 3 pgs.
"European Application Serial No. 16702237.5, Notification Regarding Rule 164 and Article 94(3) EPC dated Apr. 20, 2020", 27 pgs.
"Australian Application Serial No. 2016223288, Response filed Apr. 22, 2020 to Office Action dated Oct. 17, 2019", 8 pgs.
"Taiwanese Application Serial No. 105100428, Office Action dated Jun. 11, 2019", w English Translation, 7 pgs.

* cited by examiner

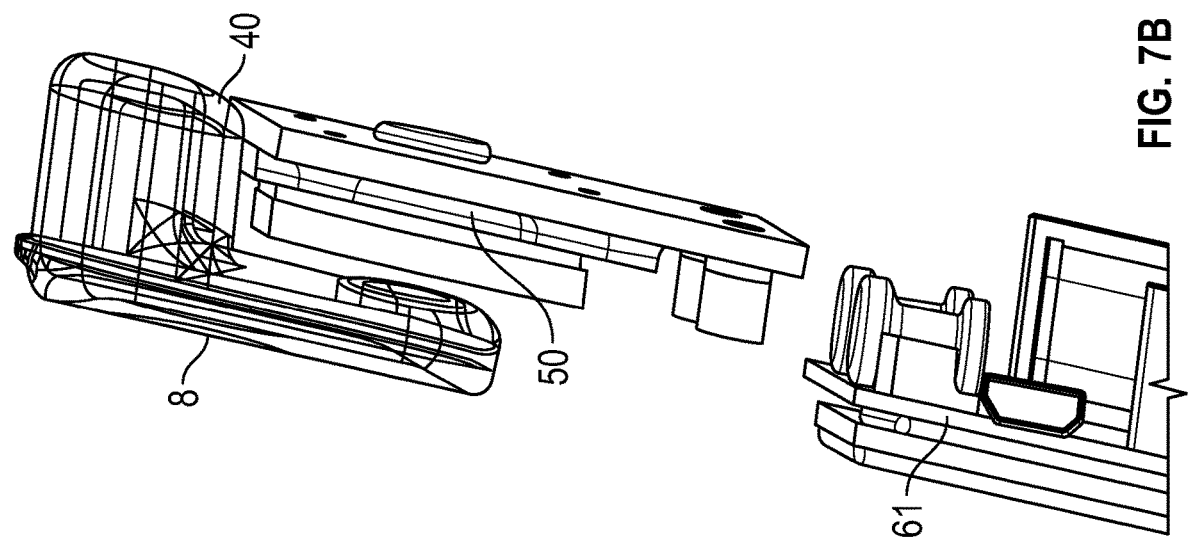
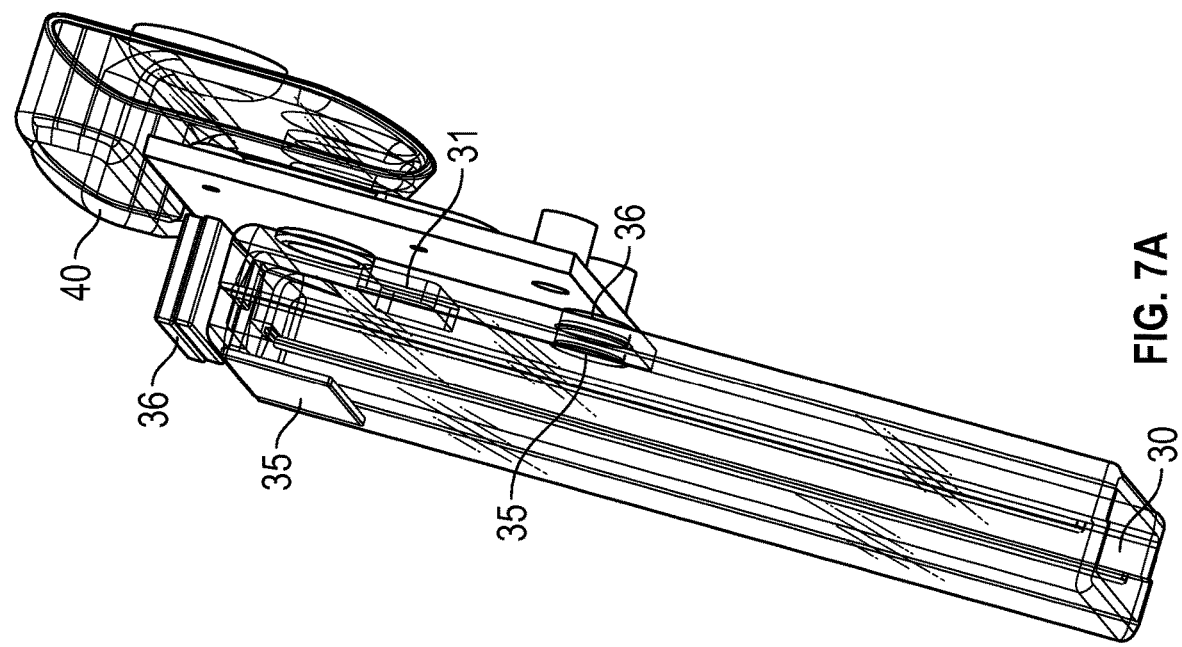
FIG. 7A
FIG. 7B

NEBULIZER DEVICE

CROSS-REFERENCE TO RELATED APPLICATION

The present application claims priority to U.S. Provisional Patent Application No. 62/101,193, filed Jan. 8, 2015, the entire content of which is hereby incorporated by reference herein.

TECHNICAL FIELD

The present invention relates to a portable nebulizer that is easy to use and provides efficient delivery of a medication to a target location.

BACKGROUND

A nebulizer is often used for delivering medications for treating respiratory diseases. A nebulizer converts a liquid medication into an aerosol, which is inhaled by the user. The deposition of the medication into the target location and the efficacy of drug delivery depend largely on the particle or droplet size and its variability. For example, if the particle size is too large, much of the medication is often deposited in the throat instead of reaching the target location such as the lungs. In addition, conventional nebulizers are often noisy, difficult to operate and large, requiring the use of tubes, face masks, external compressors, etc. These disadvantages often affect patient compliance.

There continues to be a need for nebulizers that are quiet and have improved portability, operability and delivery efficacy.

SUMMARY

In one embodiment, the present disclosure provides a portable nebulizer comprising a housing, a mouthpiece, a reservoir, a disk having multiple pores, and a unit that is configured to cause the disk to vibrate, wherein the vibration of the disk creates a pressure differential that causes a fluid from the reservoir to move through the disk to create an aerosol for delivery. In one embodiment, the mouthpiece may be held in place with at least one metal plate imbedded in the mouthpiece and at least one magnet in the housing. In certain embodiments, the reservoir may have a non-cylindrical shape. In certain embodiments, a cross section of the reservoir has a non-circular shape. In one embodiment, the nebulizer may comprise a battery and a USB port for charging the battery. In one embodiment, the nebulizer is portable and spill-proof when the reservoir is filled with a fluid. In one embodiment, the nebulizer is spill-proof when the nebulizer is being carried.

BRIEF DESCRIPTION OF THE DRAWINGS

FIG. 1 shows components of a nebulizer in accordance with an embodiment of the invention.

FIG. 2A and FIG. 2B show the front of a nebulizer in accordance with an embodiment of the invention.

FIG. 3A and FIG. 3B show the back of a nebulizer in accordance with an embodiment of the invention.

FIG. 4A and FIG. 4B show a nebulizer in accordance with an embodiment of the invention with a mouthpiece removed or attached.

FIG. 5A and FIG. 5B show the reservoir and disk of a nebulizer in accordance with an embodiment of the invention.

FIG. 6 shows a non-cylindrical-shaped reservoir in a nebulizer in accordance with an embodiment of the invention.

FIG. 7A and FIG. 7B show various components of a nebulizer in accordance with an embodiment of the invention.

FIG. 8 shows a cross section view of a nebulizer in accordance with an embodiment of the invention.

FIG. 9 shows a mouthpiece of a nebulizer in accordance with an embodiment of the invention.

FIG. 10 shows components of a nebulizer in accordance with an embodiment of the invention.

DETAILED DESCRIPTION

A nebulizer in accordance with the present disclosure has several advantages over conventional nebulizers, including portability, ease of use, universal recharging, and quiet and efficient delivery of medication. Preferably, the nebulizer in accordance with the present disclosure can be carried in a shirt or pants pocket. In one embodiment, the nebulizer is portable and spill-proof when a reservoir of the nebulizer is filled with a fluid. In one embodiment, the nebulizer is spill-proof when the nebulizer is being carried.

In one embodiment, the nebulizer in accordance with the present disclosure is free of a hose. In one embodiment, the nebulizer in accordance with the present disclosure is free of a mask. In one embodiment, the nebulizer in accordance with the present disclosure is free of a separate compressor unit.

The nebulizer in accordance with the present disclosure is easy to use. It can be loaded by simply pouring or dripping a standard packaged amount of fluid into the reservoir. In certain embodiments, the reservoir is replenishable with a second fluid. Alternatively, a pre-filled, disposable reservoir can be inserted into the nebulizer. Conventional piezoelectric nebulizers and ultrasonic nebulizers do not use pre-filled, disposable reservoirs. Compared with conventional piezoelectric nebulizers and ultrasonic nebulizers, the nebulizer of the present invention is easier to operate because a user may simply insert a pre-filled, disposable reservoir into the nebulizer. Also, the nebulizer can be operated with a single on-off switch. In certain embodiments, the nebulizer has a self-contained mouthpiece that may be flipped open without requiring additional tubes or masks. In preferred embodiments, the mouthpiece remains attached to the nebulizer and does not protrude from the nebulizer body while being carried. Also, the reservoir and mouthpiece can be removed for easy cleaning.

In one embodiment, the nebulizer may have a universal recharging feature achieved with a lithium ion battery that may be recharged using a USB port on the nebulizer. In a preferred embodiment, the battery may be recharged while the battery remains inside the nebulizer, i.e., without being removed from the nebulizer.

In preferred embodiments, the nebulizer in accordance with the present disclosure provides an aerosol with approximately 70% or more of its particles in the range considered to be respirable, described by those skilled in the art as Respirable Particle Fraction. This allows deep and efficient delivery of medication.

The dimensions and weight of the nebulizer in accordance with the present disclosure are such that it can be easily carried or moved to another location. In one embodiment, the nebulizer can be carried in a shirt or pants pocket. In one embodiment, the nebulizer is about 11.9 cm×5.4 cm×2.7 cm. In one embodiment, the total length of the nebulizer is no greater than about 20 cm. In one embodiment, the nebulizer's weight is about 98.5 g including the battery.

FIGS. 1-10 show nebulizers in accordance with embodiments of the present disclosure. The nebulizer comprises a housing 20 having a cavity for holding a reservoir 40, a mouthpiece 30, and an apparatus to nebulize fluid in the reservoir. In one embodiment, a disk 50 is provided having multiple pores, and a unit that is configured to cause the disk to vibrate so as to nebulize the fluid in the reservoir.

Figure 2A:
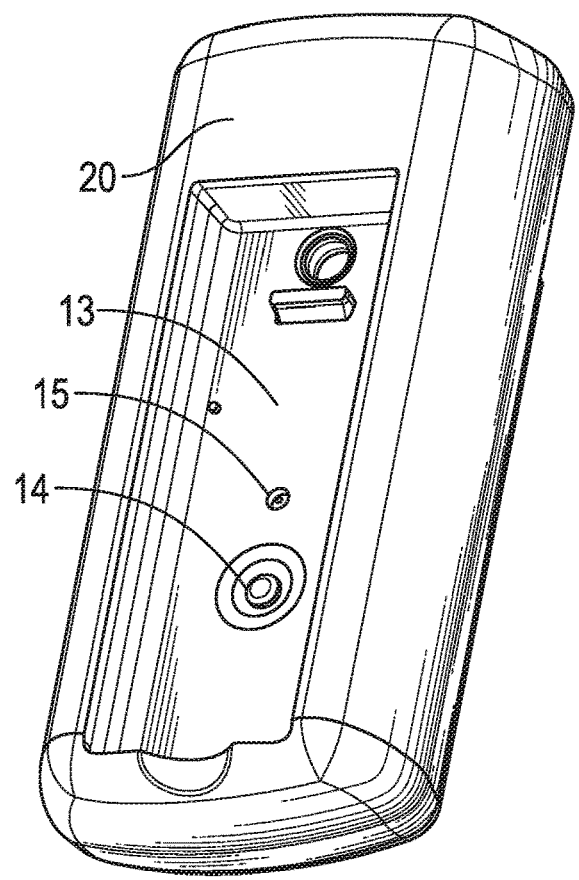
Figure 3B:
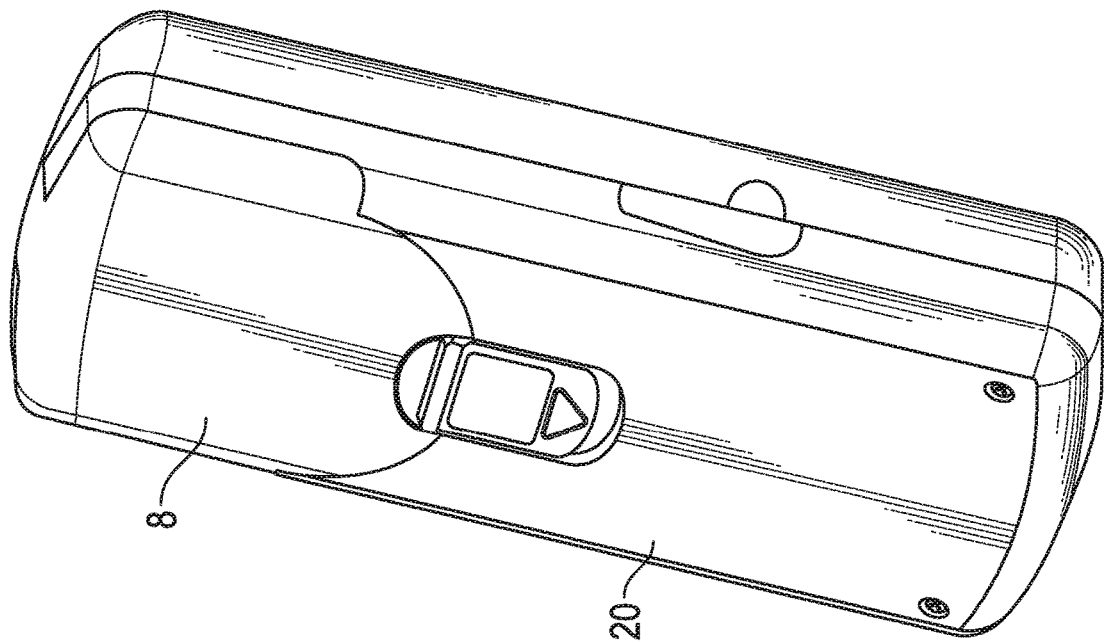
Figure 3A:
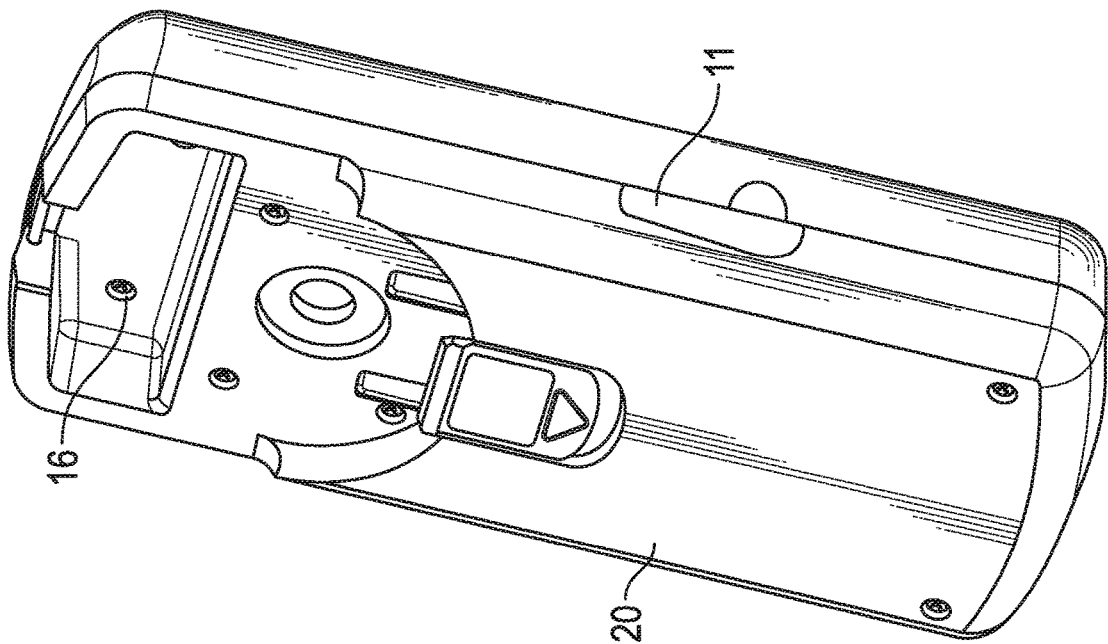
Figure 5B:
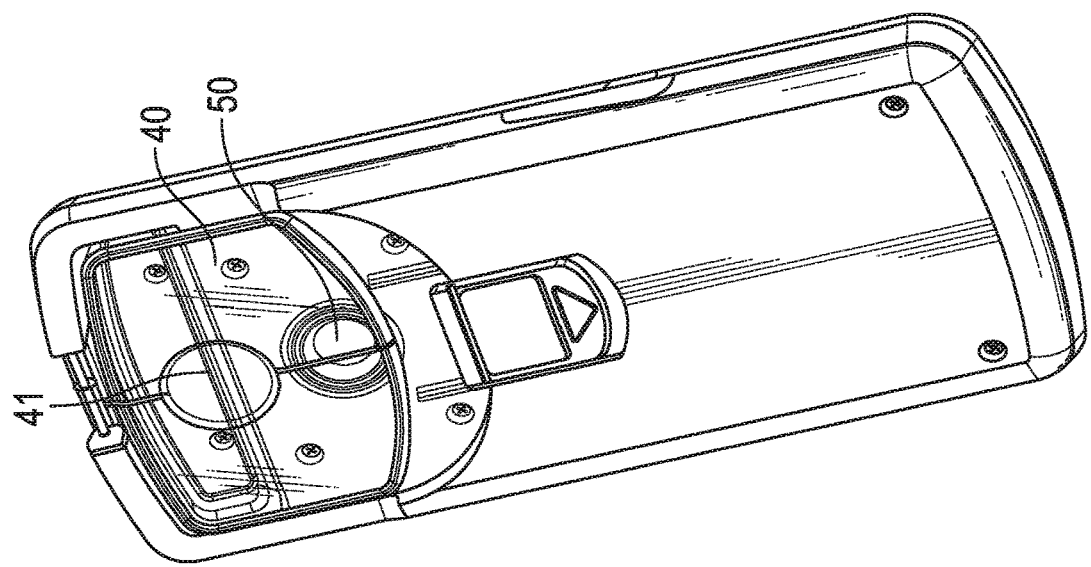
Figure 5A:
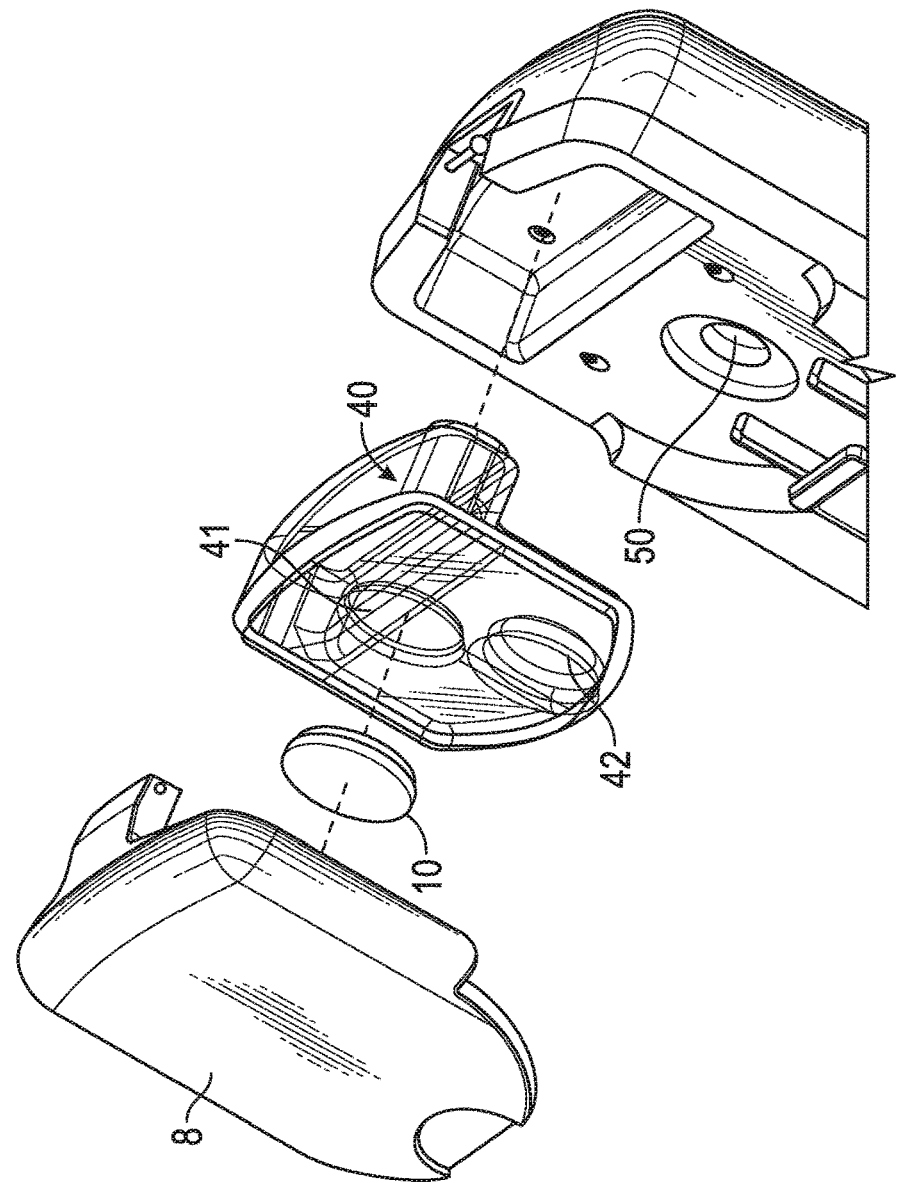

The housing 20 may comprise two molded pieces, a front cover 1 and a back cover 5, which pieces may snap together and provide a watertight seal. In one embodiment, no screws or adhesives are used. In another embodiment, at least one screw is used to hold together the front cover 1 and the back cover 5. The front cover 1 has a cavity 13 for holding the mouthpiece 30 (FIG. 2A). It may further house an on-off switch 14 and an indicator light 15 (FIG. 2A). The on-off switch 14 may comprise a flexible switch overcap 12 (FIG. 1). The indication light 15 may indicate the on/off status of the nebulizer, the battery status and/or the need to recharge the battery. The back cover 5 has a cavity 16 that holds the reservoir 40 (FIG. 3A). The nebulizer may further comprise a hinged lid 8 and a lid latch 9 (FIGS. 1 and 3A). The hinged lid 8 may snap into the back cover 5 to secure the reservoir 40 to the device and seal a fill port 41 of the reservoir 40 (FIGS. 3A, 5A and 5B). This is designed to be watertight to mitigate hazards associated with leakage.

Figure 2B:
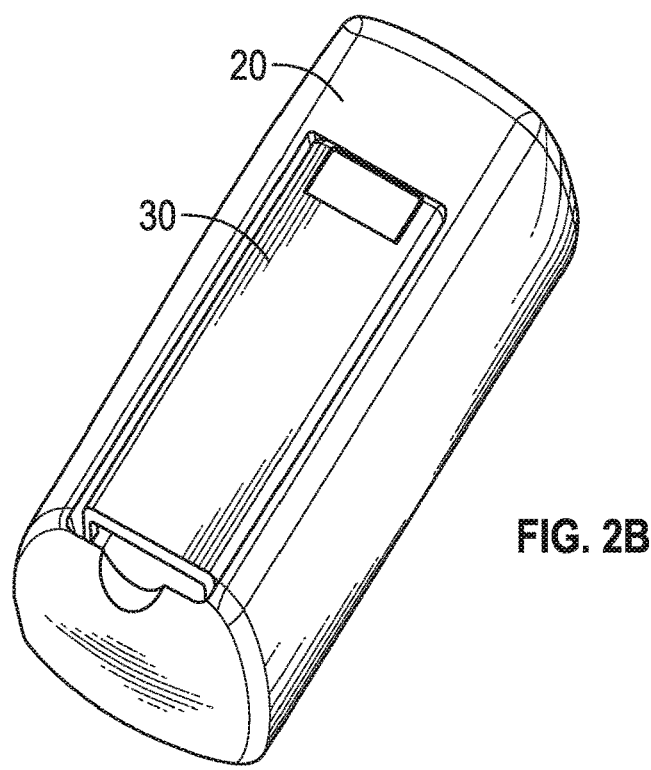
Figure 4B:
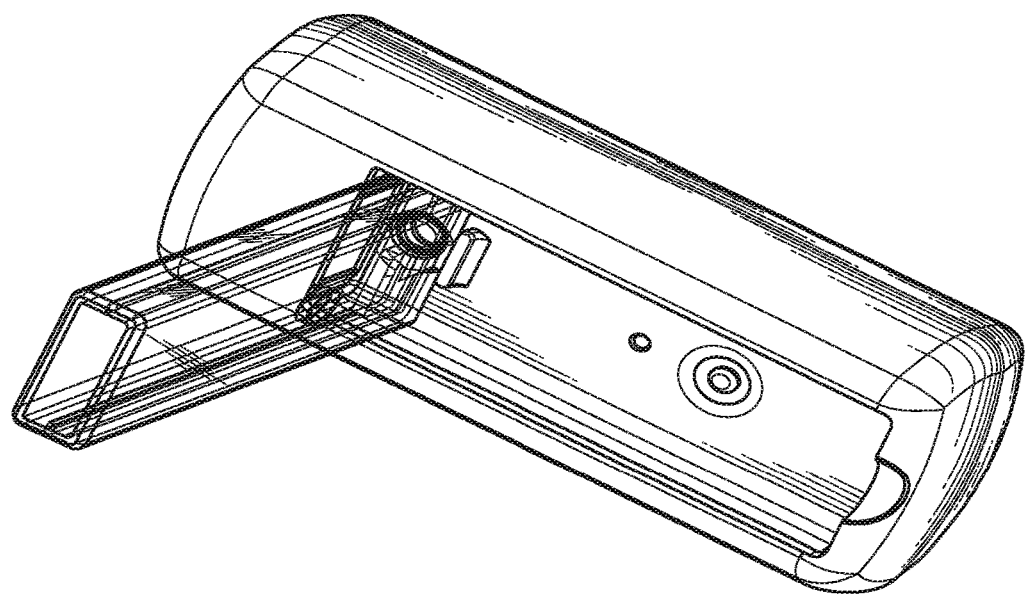
Figure 4A:
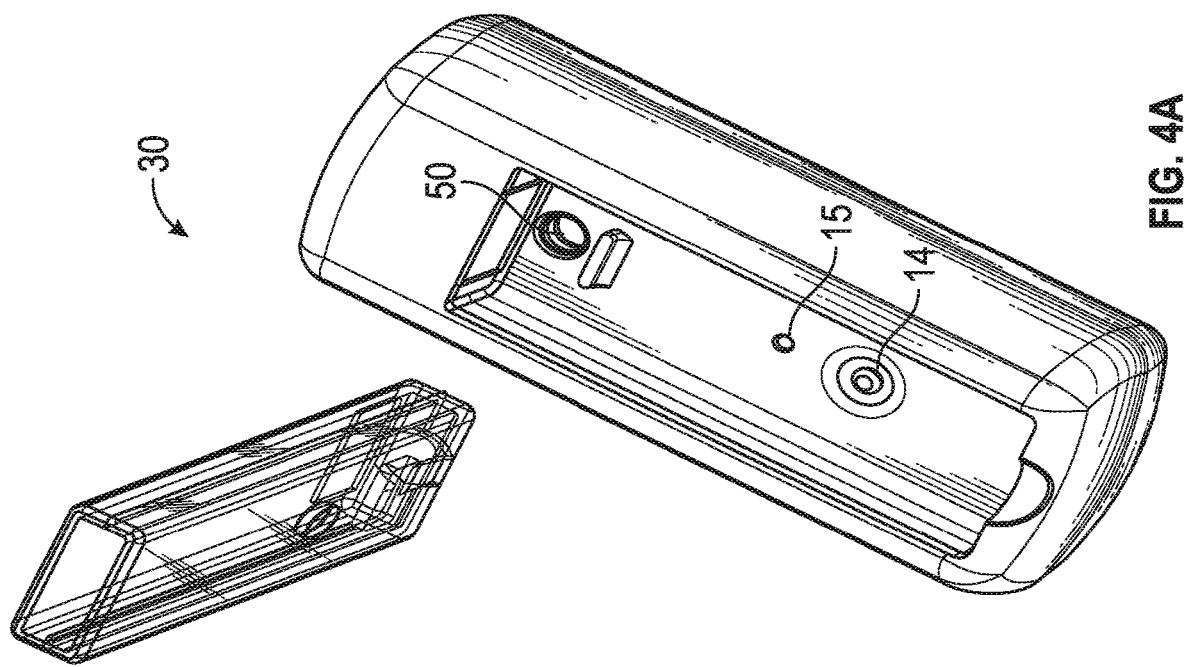
Figure 8:
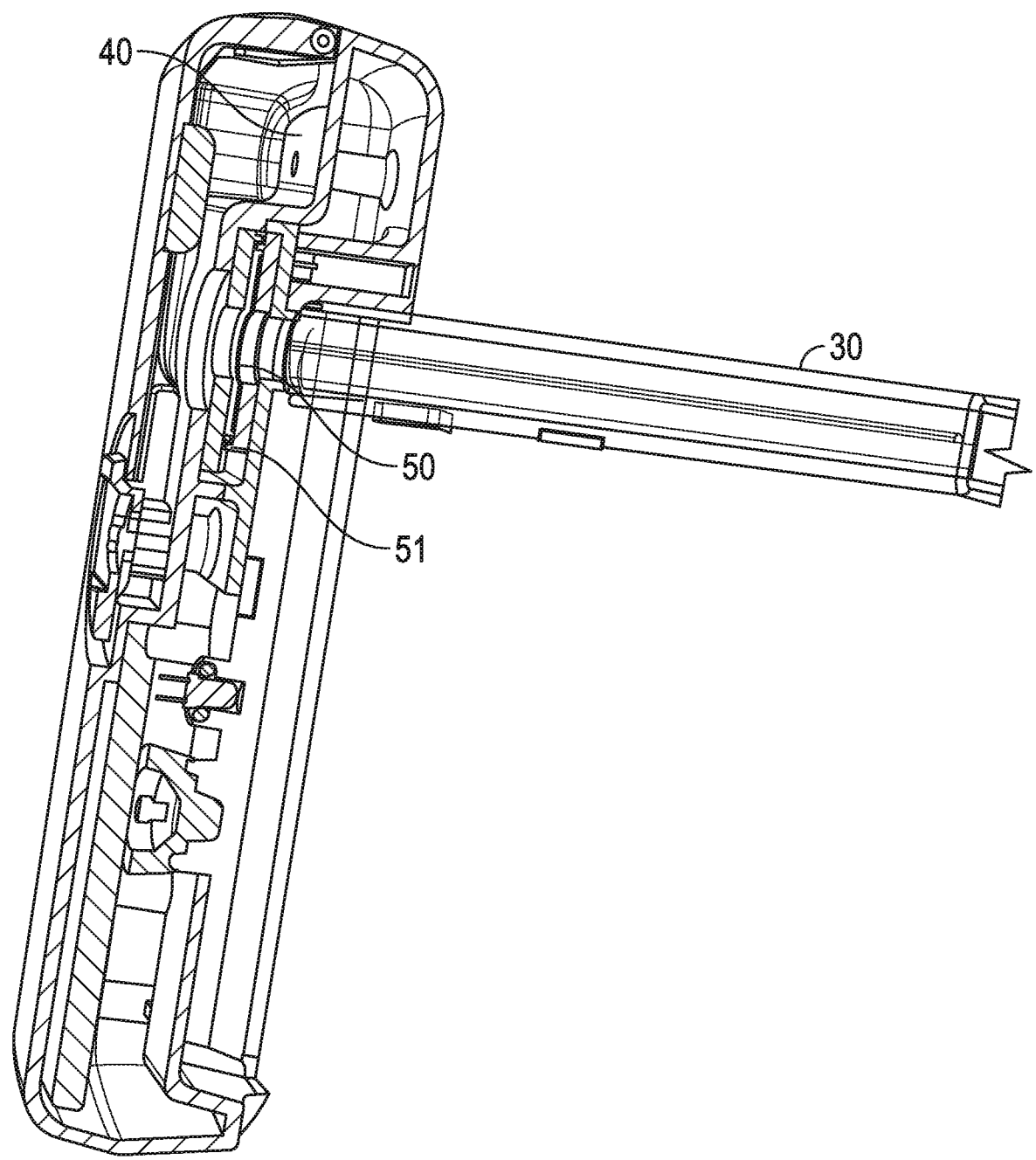

The mouthpiece 30 may comprise a top part 2 and a bottom part 3 (FIG. 1). In certain embodiments, it fits into the cavity 13 of the front cover 1 so that it does not protrude from the body of the nebulizer when it is being carried (FIGS. 2A and 2B). The mouthpiece 30 may be held in place by methods known to those skilled in the art, e.g., by using snaps or hinges, etc. In a preferred embodiment, the mouthpiece is held in place with at least one metal plate and at least one magnet. For example, the mouthpiece may be held in place with at least one imbedded metal plate 35 in the mouthpiece and at least one magnet 36 in the housing (FIGS. 7A and 9), eliminating the need for snaps or hinges. The metal plate 35 in the mouthpiece may be coated with a TEFLON® coating. The mouthpiece 30 may be in two positions, an open position (FIGS. 4B and 8) and a closed position (FIG. 2B), where it is held in place by the at least one magnet 36. In the open position, a user can inhale the aerosol through the mouthpiece 30 (FIGS. 4B and 8). In the closed position, the mouthpiece 30 is stored inside the nebulizer (FIG. 2B). In certain embodiments, the mouthpiece 30 in the closed position may be folded into or placed inside the nebulizer in a non-protruding manner, i.e., the mouthpiece 30 does not protrude from the body of the nebulizer (FIG. 2B).

Figure 9:
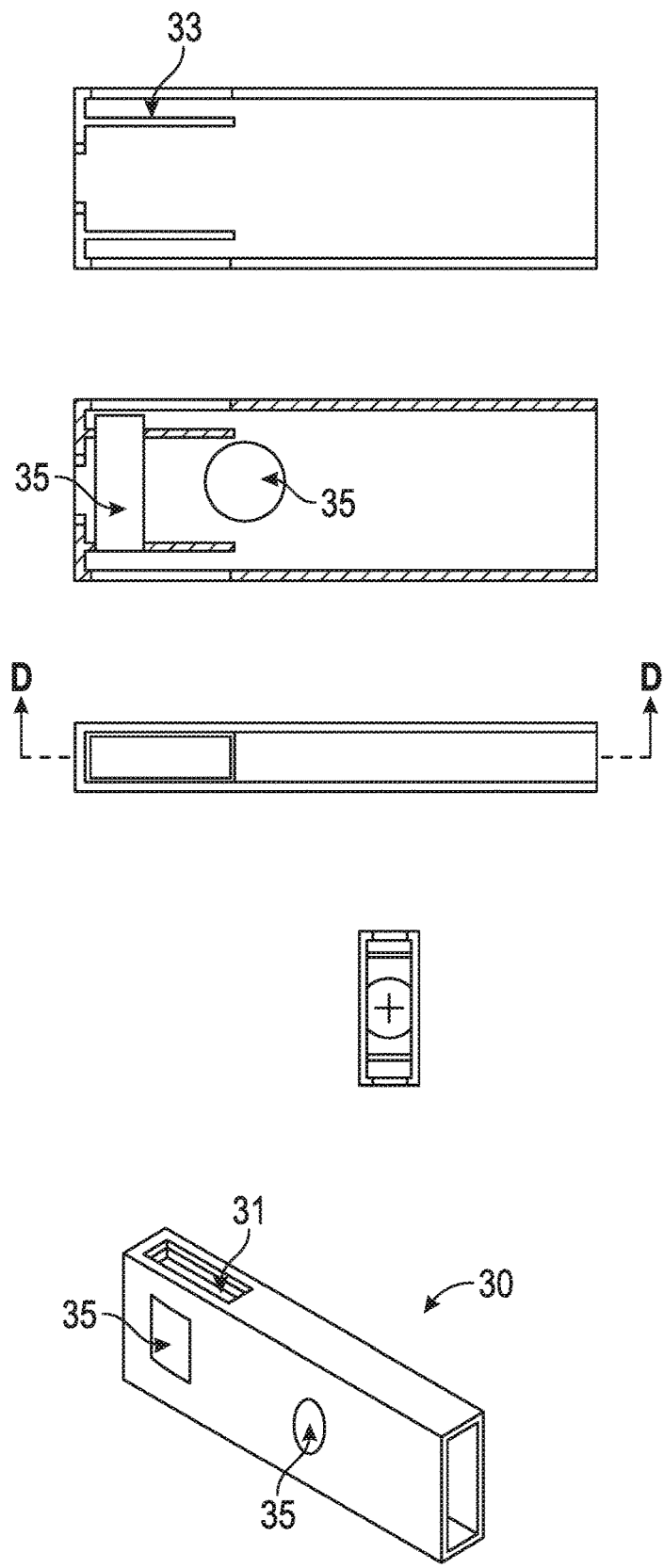
Figure 10:
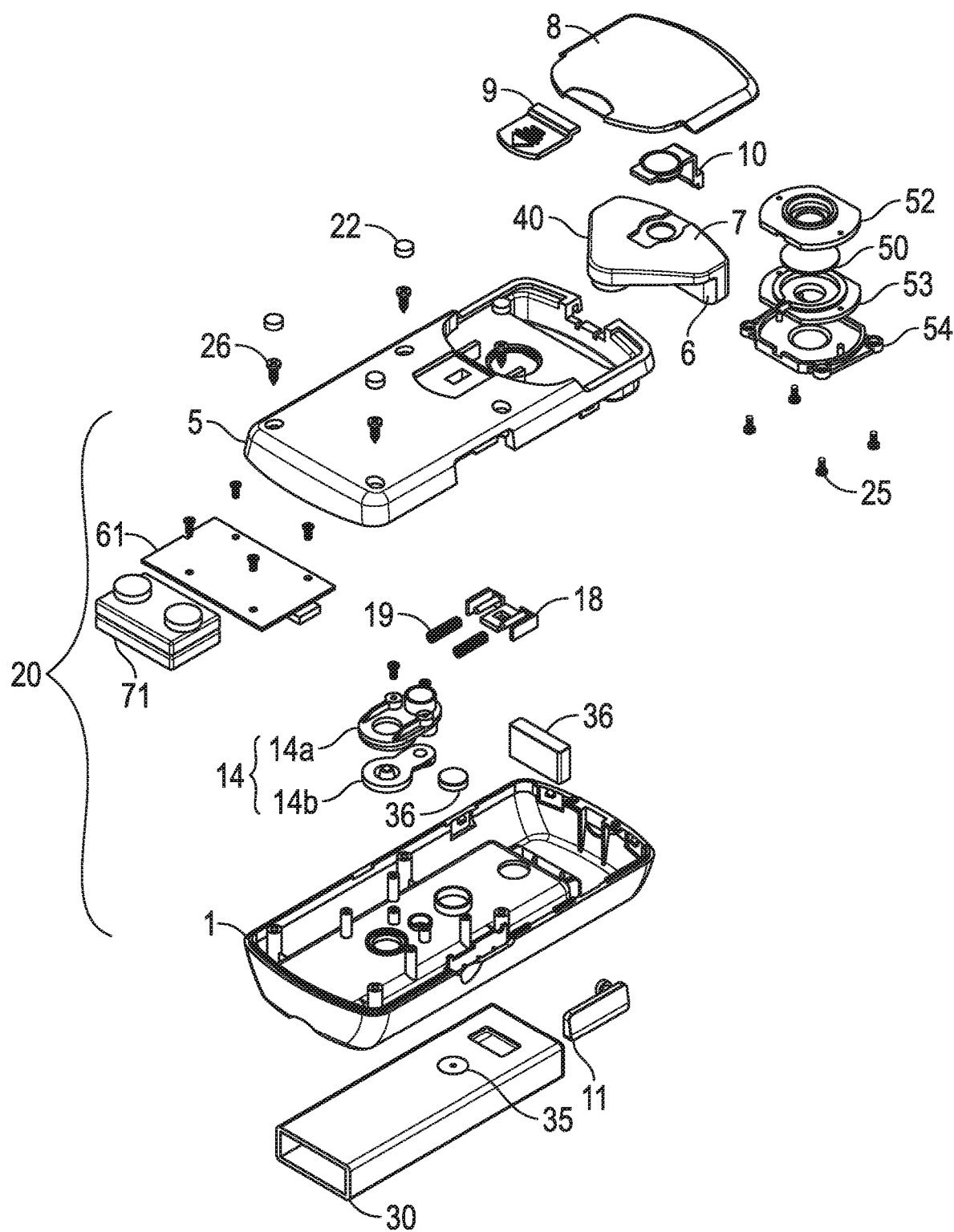

The mouthpiece 30 collects the aerosol or vapor produced by the nebulizer and delivers it to the user's mouth. The mouthpiece 30 may have at least one aperture 31 to facilitate efficient filling of the mouthpiece. For example, the mouthpiece 30 may have an aperture 31 close to one end of the mouthpiece 30 (FIG. 7A). In another embodiment, the mouthpiece 30 has two apertures 31 on two sides of the mouthpiece and two air diverters 33 inside the mouthpiece parallel to the apertures 31 (FIG. 9). The air diverters reduce turbulent air flow, prevent the aerosolized particles from condensing inside the mouthpiece, and direct the particles toward the mouth end of the mouthpiece. The mouthpiece 30 may be in a shape suitable to enhance portability and easy fitting to patients. Preferably, the mouthpiece 30 is rectangular or tubular. For cleaning, the mouthpiece may be removed with a simple tug and cleaned with running, hot tap water. In some embodiments, the mouthpiece may be disinfected with 70% ethyl alcohol for about one minute.

Figure 6:
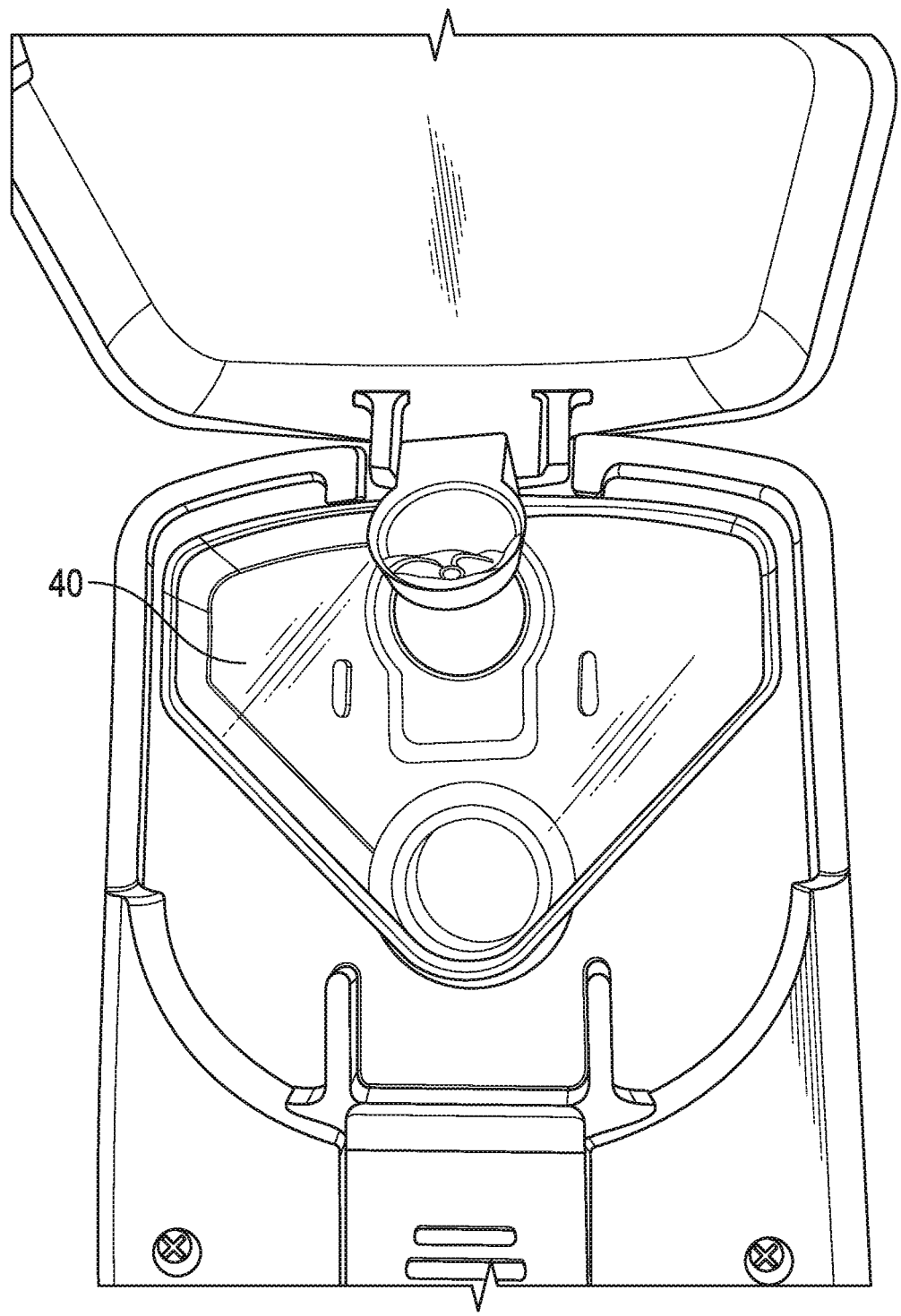

The reservoir 40 holds a fluid that is turned into an aerosol or vapor by the nebulizer and delivered to the user. The fluid may contain a pharmaceutically active ingredient. The reservoir 40 may comprise a front part 6 and a back part 7 (FIG. 1). The reservoir 40 may contain a fill port 41 for loading the fluid and a channel 42 that feeds the fluid to the disk 50 (FIGS. 5A and 5B). In a preferred embodiment, the reservoir is shaped to allow the fluid to flow freely to the face of the vibrating disc. Conventional nebulizers have a medication cup that is cylindrical with a circular cross section. In certain embodiments, the reservoir has a shape that depletes a residual volume of the reservoir. In certain embodiments, the reservoir has a non-cylindrical shape as shown in FIG. 6. This shape would help draw liquid to the disk through capillary action, reduce the amount of the residual fluid left in the reservoir and improve delivery efficiency. In certain embodiments, a cross section of the reservoir has a non-circular shape. In certain embodiments, a cross section of the reservoir has an irregular pentagonal shape that is defined by five angles, wherein one of the five angles of the irregular pentagonal shape is smaller than other four angles, such that a portion of the irregular pentagonal shape is a protrusion defined by the one of the five angles (FIG. 6). This shape provides capillary action, allows even flow and reduces the amount of residual fluid at the end of a nebulization treatment.

Preferably, the internal volume of the reservoir is 3 ml-6 ml. More preferably, the internal volume of the reservoir is 5 ml.

The reservoir 40 may be made of materials that are nontoxic and inert to the fluid contained in the reservoir. For example, it may be made of polycarbonate resin. Preferably, it is made of LEXAN polycarbonate resin.

The reservoir 40 may be filled with a package containing a predetermined amount of the fluid. In one embodiment, the package may contain a single unit dose of pharmaceutical active ingredient. Alternatively, the reservoir 40 may be disposable and allow another pre-packaged reservoir to be inserted into the nebulizer. In one embodiment, a reservoir plug/stopper 10 is integrated into the hinged lid 8 for ease of use (FIG. 1).

The disk 50 has multiple pores at its center. In certain embodiments, the disk has about 1,000 to 2,800 pores, preferably about 1,000-1,200, depending on the material used for the disk. The disk may be made of any suitable materials. For example, the disk may be made of stainless steel, preferably medical grade stainless steel. In another embodiment, the disk is made of an alloy of nickel (Ni) and cobalt (Co). The size of the pores may range from about 4 to 5 microns. In certain embodiments, the pores are round or substantially round, and the size of the pores means the diameter of the pores. The disc 50 may be sandwiched between an outflow port of the reservoir 40 and an exit port in the front cover 1 of the housing 20. The nebulizer may comprise a component 4 surrounding the disk (FIG. 1). In certain embodiments, the nebulizer may comprise at least one disk compression brace 51 (FIG. 8).

The disk 50 is caused to vibrate at a high frequency in the direction of the fluid only, increasing the pressure on that side of the disk, creating a pressure differential that causes the fluid to move through the disk to create an aerosol for delivery. The disk may vibrate at a frequency ranging from 100 kilohertz (kHz) to 200 kHz. Preferably, the disk vibrates at a frequency of about 110 kHz. The amplitude of the vibration may be AC 80v. In certain embodiments, the resultant aerosol has a particle or droplet size considered by those skilled in the art to be a respirable particle dose. In certain embodiments, the disk vibrates creating a pressure differential that forces the fluid through 4 to 5 micron holes that aerosolize the fluid into respirable droplets. The vibration of the disk 50 creates an aerosol or vapor that is fed into the mouthpiece 30 for inhalation. This process is different from conventional ultrasonic nebulizers that fire ultrasonic waves at the fluid to vaporize the surface of the fluid.

The nebulizer may comprise a power source for providing energy for operating the nebulizer. For example, the power source may be a battery 71, such as a lithium ion battery or other rechargeable batteries. Preferably, the battery is a lithium ion battery. In one embodiment, the battery may be recharged while the battery remains inside the nebulizer, i.e., without being removed from the nebulizer. In one embodiment, the battery allows at least 60 minutes of use. The battery may be rechargeable. Preferably, the battery may be charged through a USB port, which may be covered by a plug 11 (FIGS. 1 and 3A) when not in use. The USB port may have a watertight seal. In one embodiment, the USB port may be sandwiched between the front cover 1 and the back cover 5 on the side of the nebulizer. The USB port allows universal charging, which provides further convenience for the user.

In certain embodiments, the unit that is configured to cause the disk 50 to vibrate may comprise a PCB 61 (FIG. 7B).

In one embodiment, the nebulizer may further comprise a timer. The nebulizer may contain a control unit that is configured to give a time-limited treatment. This feature allows a patient to adjust the amount of the fluid that is nebulized and delivered. For example, a patient may take the full amount of a single dose of the fluid contained in the reservoir 40 by keeping the nebulizer on for a certain period of time or take a fraction (e.g., one-third) of the single dose of the fluid contained in the reservoir 40 by keeping the nebulizer on for a corresponding fraction (e.g., one-third) of said period of time. As such, the fluid in the reservoir 40 may comprise a single dose of a pharmaceutically active ingredient or multiple fractional doses of the active ingredient. A patient using the nebulizer may titrate the dose based on time.

The fluid contained in the reservoir 40 may be an aqueous solution, suspension, mixture, or formulation containing a solvent or free of a solvent. In certain embodiments, the fluid may comprise a pharmaceutically active ingredient. The active ingredients that may be used include albuterol, albuterol and ipratropium, arformoterol tartrate, budesonide, colistimethate, cromolyn sodium, dexamethasone, dornase alpha, fluticasone, formoterol, ipratropium bromide, levalbuterol, mometasone and formoterol, and tobramycin.

FIG. 10 shows components of a nebulizer in accordance with an embodiment of the invention. The nebulizer comprises a housing 20, a mouthpiece 30, a reservoir 40, a disk 50 having multiple pores, a PCB unit 61 that is configured to cause the disk to vibrate, and a rechargeable battery 71. The housing 20 comprises a front cover 1 and a back cover 5, which are held together by screws 26. The screws 26 are covered by plugs 22. The front cover 1 has a cavity for holding the mouthpiece 30 in such a manner that the mouthpiece 30 does not protrude from the body of the nebulizer. The mouthpiece 30 is held in place with at least one imbedded metal plate 35 in the mouthpiece and at least one magnet 36 in the housing. A pre-filled, disposable reservoir 40 can be inserted into the nebulizer. The reservoir 40 comprises a front part 6 and a back part 7. A reservoir plug/stopper 10 seals the reservoir 40 so that it is spill-proof. In this embodiment, a cross section of the reservoir has an irregular pentagonal shape that is defined by five angles, wherein one of the five angles of the irregular pentagonal shape is smaller than other four angles, such that a portion of the irregular pentagonal shape is a protrusion defined by the one of the five angles. This shape of the reservoir allows even flow and reduces the amount of residual fluid at the end of a nebulization treatment. The disk 50 is surrounded by a gasket comprising a gasket top 52, a gasket bottom 53 and a gasket cover 54, which are held together by screws 25. The battery 71 is rechargeable in place inside the nebulizer via a USB port, which is covered by a USB plug 11 when the USB port is not being used. The front cover 1 houses an on-off switch 14, which comprises a switch cover 14*a* and a switch actuator 14*b*. Also, the nebulizer comprises a hinged lid 8 and a lid latch 9. The lid latch 9 is movable through at least one spring 19 and a spring holder 18.

While various embodiments have been described, other embodiments are plausible. It should be understood that the foregoing descriptions of various examples of nebulizers are not intended to be limiting, and any number of modifications, combinations, and alternatives of the examples may be employed.

The embodiments described herein are merely illustrative, as numerous other embodiments may be implemented without departing from the spirit and scope of the present invention. Moreover, while certain features of the invention may be described above only in the context of certain examples or configurations, these features may be exchanged, added, and removed from and between the various embodiments or configurations while remaining within the scope of the invention.

The invention claimed is:

1. A nebulizer comprising:

a housing having a cavity;

a reservoir within the housing for holding a fluid;

a mouthpiece;

a disk with multiple pore in communication with the fluid and configured to nebulize the fluid; and wherein the mouthpiece is removably connected to the housing and in communication with the disk;

wherein the mouthpiece is disposed to be withdrawn entirely from the cavity in a closed state and repositioned in the cavity in an open state, wherein the mouthpiece is flush with the housing in the closed state; wherein a cross section of the reservoir has an irregular pentagonal shape that is defined by five angles, wherein one of the five angles of the irregular pentagonal shape is smaller than other four angles, such that a portion of the irregular pentagonal shape is a protrusion defined by the one of the five angles and oriented with smallest angle at bottom to promote full usage of fluid in the reservoir.

2. The nebulizer of claim 1, wherein the mouthpiece is held in place with at least one metal plate imbedded in the mouthpiece and at least one magnet in the housing.

3. The nebulizer of claim 1, wherein the mouthpiece has two apertures on two sides of the mouthpiece and two air diverters inside the mouthpiece parallel to the apertures.

4. The nebulizer of claim 1, wherein the mouthpiece has one aperture on a side of the mouthpiece and no air diverter.

5. The nebulizer of claim 1, wherein the disk is configured to vibrate to create a pressure differential to nebulize the fluid.

6. The nebulizer of claim 1, wherein the nebulizer further comprises a timer, and wherein the timer allows a portion of the fluid in the reservoir to be aerosolized upon a single actuation of the nebulizer.

7. The nebulizer of claim 1, wherein the mouthpiece is pivotally connected to the housing with a magnet.

8. The nebulizer of claim 1, further comprising a rechargeable battery configured to be recharged within the nebulizer.

9. The nebulizer of claim 8, wherein the nebulizer further comprises a USB port for charging the battery.

10. A method, comprising:
powering on a nebulizer, the nebulizer comprising:
a housing having a cavity;
a reservoir within the housing for holding a fluid;
a mouthpiece;
a disk with multiple pore in communication with the fluid and configured to nebulize the fluid; and
wherein the mouthpiece is removably connected to the housing and in communication with the disk;
wherein the mouthpiece is disposed to be withdrawn entirely from the cavity in a closed state and repositioned in the cavity in an open state,
wherein an exterior side of the mouthpiece flush with the housing in the closed state;
removing the mouthpiece from the housing in the closed state and repositioning the mouthpiece into the cavity in the open state; wherein a cross section of the reservoir has an irregular pentagonal shape that is defined by five angles, wherein one of the five angles of the irregular pentagonal shape is smaller than other four angles, such that a portion of the irregular pentagonal shape is a protrusion defined by the one of the five angles and oriented with smallest angle at bottom to promote full usage of fluid in the reservoir; and
nebulizing the fluid with the disk.

11. The method of claim 10, wherein the mouthpiece is held in place with at least one metal plate imbedded in the mouthpiece and at least one magnet in the housing.

12. The method of claim 10, wherein the mouthpiece has two apertures on two sides of the mouthpiece and two air diverters inside the mouthpiece parallel to the apertures.

13. The method of claim 10, wherein the mouthpiece has one aperture on a side of the mouthpiece and no air diverter.

14. The method of claim 10, wherein the vibrating the disk creates a pressure differential to nebulize the fluid.

15. The method of claim 10, further comprising
a battery that is rechargeable while the battery is placed inside the nebulizer.

16. The method of claim 15, wherein the nebulizer further comprises a USB port for charging the battery, the method further comprising charging the battery.

17. A nebulizer comprising:
a housing having a cavity;
a reservoir within the housing for holding a fluid;
a mouthpiece having multiple surfaces and an outlet;
a disk with multiple pore in communication with the fluid and configured to nebulize the fluid; and
wherein the mouthpiece is pivotally connected to the housing and in communication with the disk;
wherein the mouthpiece is configured to pivot between an open and closed state,
wherein the mouthpiece is configured to rotate into the housing in the closed state;
wherein the outlet is enclosed within the cavity in the closed state: wherein a cross section of the reservoir has an irregular pentagonal shape that is defined by five angles, wherein one of the five angles of the irregular pentagonal shape is smaller than other four angles, such that a portion of the irregular pentagonal shape is a protrusion defined by the one of the five angles and oriented with smallest angle at bottom to promote full usage of fluid in the reservoir.

* * * * *